(12) United States Patent
Brain et al.

(10) Patent No.: US 7,360,540 B2
(45) Date of Patent: Apr. 22, 2008

(54) ENDOTRACHEAL TUBE WHICH PERMITS ACCURATE DETERMINATION OF MUCOSAL PRESSURE

(75) Inventors: Archibald I. J. Brain, Les Bons Villers (BE); Peter Jeffrey Young, King's Lynn (GB)

(73) Assignee: Indian Ocean Medical Inc., Mahe (SC)

( * ) Notice: Subject to any disclaimer, the term of this patent is extended or adjusted under 35 U.S.C. 154(b) by 1197 days.

(21) Appl. No.: 10/144,397

(22) Filed: May 13, 2002

(65) Prior Publication Data

US 2003/0136413 A1  Jul. 24, 2003

Related U.S. Application Data

(60) Provisional application No. 60/351,128, filed on Jan. 23, 2002.

(51) Int. Cl.
*A61M 16/00* (2006.01)
*A62B 9/06* (2006.01)

(52) U.S. Cl. ............................. 128/207.14; 128/200.26

(58) Field of Classification Search ..............................
128/207.14–207.18, 911–912, 200.26; 606/199;
604/96.01, 93.01, 95.03–95.04, 97.01, 101.01–101.03
See application file for complete search history.

(56) References Cited

U.S. PATENT DOCUMENTS

| | | | | |
|---|---|---|---|---|
| 3,407,817 A | | 10/1968 | Galleher, Jr. ................. 128/351 |
| 3,734,100 A | * | 5/1973 | Walker et al. ......... 128/207.15 |
| 3,884,242 A | * | 5/1975 | Bazell et al. .......... 128/207.15 |
| 4,341,210 A | * | 7/1982 | Elam ...................... 128/207.15 |
| 5,447,497 A | * | 9/1995 | Sogard et al. ......... 604/101.02 |
| 5,803,080 A | * | 9/1998 | Freitag .................. 128/207.14 |
| 5,957,134 A | | 9/1999 | Lee ........................ 128/207.14 |
| 5,976,153 A | * | 11/1999 | Fischell et al. ............. 623/1.11 |
| 6,093,142 A | * | 7/2000 | Ciamacco, Jr. ................. 600/3 |
| 6,553,993 B2 | * | 4/2003 | Toti et al. .............. 128/207.14 |
| 6,723,113 B1 | * | 4/2004 | Shkolnik ..................... 606/194 |

FOREIGN PATENT DOCUMENTS

| | | |
|---|---|---|
| GB | 1399093 | 6/1975 |
| GB | 1414344 | 11/1975 |
| GB | 1526286 | 9/1998 |
| GB | 2324735 | 11/1998 |

* cited by examiner

*Primary Examiner*—Teena Mitchell
*Assistant Examiner*—Kristen C. Matter
(74) *Attorney, Agent, or Firm*—Wilmer, Cutler, Pickering, Hale and Dorr LLP

(57) ABSTRACT

The disclosed endotracheal tube includes a silicone tubular member that has a proximal end, a distal end, and a lumen extending through the member to supply air from the proximal end to the distal end. The tubular member defines a first zone and a second zone. At least a portion of the first zone has a first outer diameter. The second zone has a second outer diameter. The first outer diameter is less than the second outer diameter. The first and second zones are adjacent to one another and are configured for insertion into the trachea of a human patient. A silicone cuff is attached to the tubular member such that the cuff extends over at least a portion of the first zone. The silicone cuff is mounted such that when the cuff is inflated in a trachea, the cuff reaches its plateau pressure prior to circumferentially contacting the inner wall of the trachea so that an accurate pressure reading may be taken of the pressure the cuff exerts on an inner wall of the trachea.

30 Claims, 8 Drawing Sheets

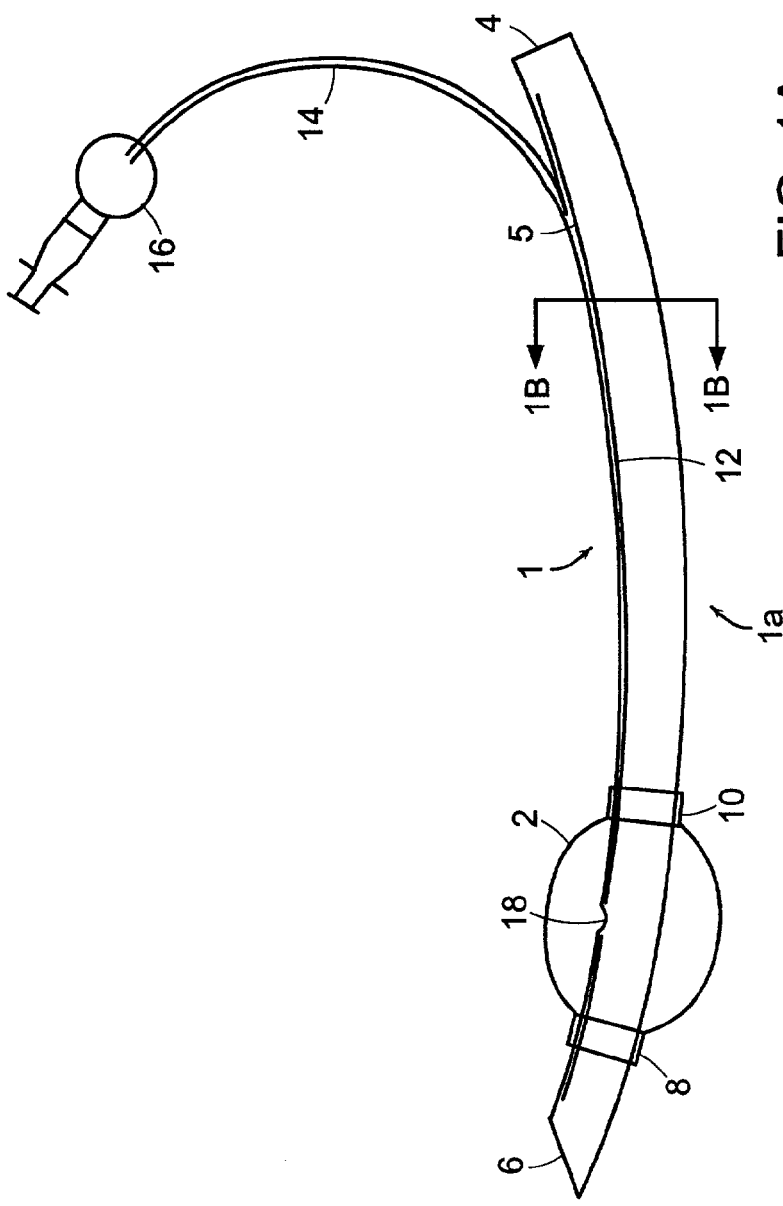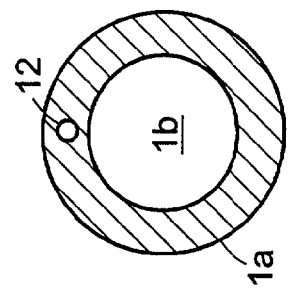
FIG. 1A
PRIOR ART
FIG. 1B

PV DIAGRAM
LATEX BALLOON ON STANDARD TUBE

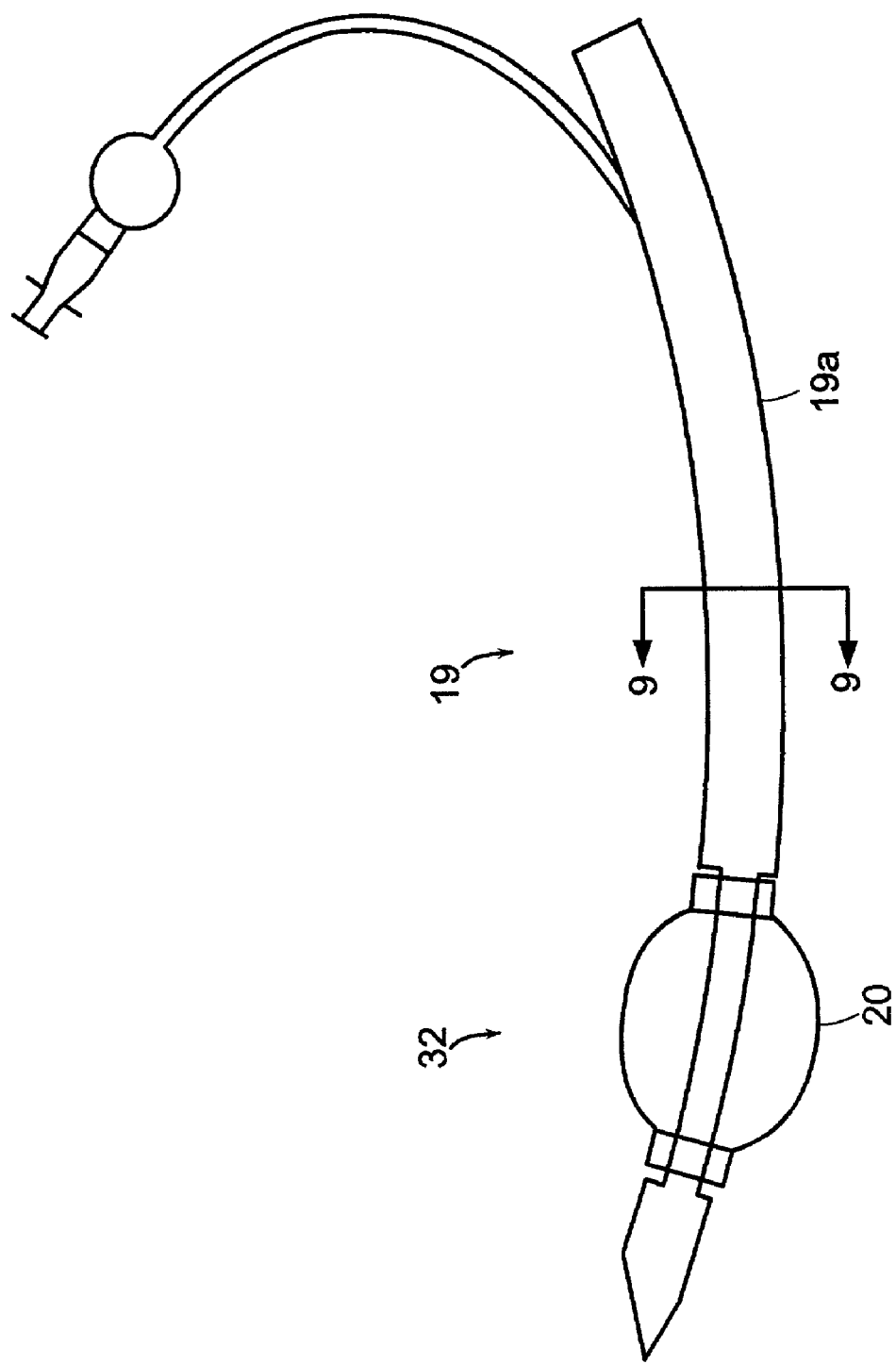

ENDOTRACHEAL TUBE WHICH PERMITS ACCURATE DETERMINATION OF MUCOSAL PRESSURE

BACKGROUND OF THE INVENTION

The present invention relates to an endotracheal tube. More specifically, the present invention relates to an endotracheal tube, which permits accurate determination of the pressure exerted by the endotracheal tube's sealing cuff against the tracheal wall.

FIG. 1A shows a prior art endotracheal tube (ETT) 1. FIG. 1B shows a magnified sectional view of ETT 1 taken along line 1B-1B as shown in FIG. 1A. ETT 1 includes a semi-rigid hollow tube 1a, which extends from a proximal end 4 to a distal end 6. Tube 1a is made from poly-vinyl-chloride (PVC). ETT 1 further includes an inflatable balloon, or cuff, 2 mounted near distal end 6. Balloon 2 is sealed to hollow tube 1a at locations 8 and 10 to form an airtight space within the balloon. ETT 1 further includes a central airway lumen 1b, which extends from the proximal end 4 to the distal end 6 of hollow tube 1a. Hollow tube 1a further defines a small inflation lumen 12, which extends through the wall of hollow tube 1a. Inflation lumen 12 provides an opening 18 near its distal end within the interior volume of the balloon 2. At location 5, near the proximal end of hollow tube 1a, the inflation lumen 12 is connected to an inflation line, or tube, 14. An air syringe 16, or other suitable air supply, connected to the proximal end of inflation line 14 selectively controls inflation and deflation of balloon 2. FIG. 1A shows balloon 2 in an inflated condition.

In operation, the distal end 6 of ETT 1 is inserted into the mouth of an unconscious patient, through the patient's natural airway, until the distal end 6 extends into the patient's trachea. The proximal end 4 remains outside the patient. Balloon 2 is in a deflated condition while distal end 6 is being inserted into the patient. After distal end 6 has been positioned within the trachea, balloon 2 is inflated (e.g., by syringe 16) until the outer wall of balloon 2 forms a seal with the inner mucosal lining of the trachea. Once such a seal has been established, a ventilator coupled to the proximal end 4 of ETT 1 may be used to apply intermittent positive-pressure ventilation (IPPV) to the patient. During IPPV, medical gasses supplied to the proximal end 4 of ETT 1 by the ventilator effectively forces the gasses through airway lumen 1b and into the patient's lungs. However, if a seal is not established between balloon 2 and the interior lining of the trachea, gas forced out of distal end 6 simply escapes through the space between balloon 2 and the interior lining of the trachea, and out of the patient's mouth, instead of being forced into the patient's lungs.

Balloon 2 is often constructed from a relatively inelastic material, e.g., PVC. Such inelastic balloons in their inflated condition rarely fit the tracheal diameter exactly. For example, if a patient's trachea is smaller than the expanded size of the balloon, the balloon forms wrinkles at the interface of the balloon and the inner wall of the trachea resulting in an imperfect seal. For example, during long term placement of the ETT, the wrinkles, or micro-leaks, permit fluid and other material to pass between the inflated cuff and the inner lining of the trachea and into the lungs. If, on the other hand, the expanded balloon is too small for the tracheal diameter, no seal will be achieved between the balloon and the inner lining of the trachea. Hence, in practice, since the tracheal diameter is rarely known precisely, the balloon size is always chosen to be larger than the largest expected tracheal diameter. Micro-leaks with such inelastic cuff materials are therefore inevitable.

A further problem attends the use of such plastic ETT cuffs, as noted by Young et al. in GB2324735. When the cuff is inflated within a patient, the pressure within the cuff, or the "intra-cuff pressure", can be functions of:
1. resistance of the cuff material to stretching;
2. resistance of the tracheal wall to expansion of the cuff; or
3. a mixture of both factors.

The intra-cuff pressure may be easily measured by, for example, a pressure gauge coupled to the inflation line 14. However, although it is easy to measure the intra-cuff pressure, it is not easy to know how much each of the three above factors contribute to that pressure. Clinically, it is of vital importance to prevent the outer wall of the cuff from applying excessive pressure against the delicate inner lining of the tracheal wall. For convenience of exposition, the term "mucosal pressure" will be used herein to refer to the pressure applied by the outer wall of the inflated cuff to the inner lining of the trachea. If the mucosal pressure is too high, the trachea may become dilated and/or circulation may be cut off in the trachea, which may lead to necrosis of the tissue. In general, the mucosal pressure should be kept below a pressure of thirty centimeters of water. Excessive mucosal pressure caused by over inflation of the cuff can result if there is no feedback to the clinician about the intra-cuff pressure. Additionally, even if the intra-cuff pressure is known, the mucosal pressure generally remains unknown.

In order to overcome this problem, Young et al. in GB2324735, teach the use of a cuff made of a more elastic material such as latex or silicone. An important characteristic of elastic materials such as latex or silicone is that when a sheet of either material is stretched, a point is reached after which the material provides no further resistance to further stretching. When a balloon or cuff formed from elastic material such as latex or silicone is inflated, the intra-cuff pressure initially increases as the volume of the inflated cuff increases. However, with continued inflation the cuff material eventually reaches the point at which it offers no further resistance to stretching. After this point, continued inflation of the cuff causes further expansion of the cuff without a corresponding increase in intra-cuff pressure. In other words, when such an elastic cuff is inflated, the intra-cuff pressure increases initially but then reaches a plateau, and further inflation increases the cuff's volume without causing the intra-cuff pressure to exceed the pressure plateau.

FIG. 2A graphically illustrates the inflation characteristics of an elastic cuff made of latex or silicone. As the volume of gas introduced into the cuff increases from zero to value C, the intra-cuff pressure increases from zero to value A. However, once an intra-cuff pressure of A is achieved, further inflation increases the volume of the expanded cuff, at least to the value D, without raising the intra-cuff pressure. Accordingly, the level A is a pressure plateau. Continued inflation to expand the volume of the balloon beyond value D may eventually cause additional increases in intra-cuff pressure and a final bursting of the balloon. However, the pressure plateau A is not exceeded when the volume is in the range between values C and D.

Young et al. in GB 2324735 teach constructing the cuff of an ETT such that it reaches its pressure plateau before it has expanded sufficiently to circumferentially contact the tracheal walls (i.e., before it has expanded sufficiently to cause contact between the cuff and the inner lining of the trachea along the entire circumference of the trachea). Since the pressure plateau for the cuff is a known constant, when the balloon is inflated to the pressure plateau before it circumferentially contacts the tracheal wall, any additional increase in the intra-cuff pressure (i.e. increase in the pressure within the cuff beyond the pressure plateau), will be caused by contact between the balloon and the trachea (i.e. by the tracheal wall resisting additional expansion of the balloon). Thus, the mucosal pressure can be accurately determined by subtraction (i.e., under these conditions, the mucosal pressure equals the difference between the current intra-cuff pressure and the pressure plateau). Determination, or monitoring, of the mucosal pressure enables avoidance of potentially damaging mucosal pressures.

FIG. 2B graphically illustrates measurement of the mucosal pressure for a latex cuff. FIG. 2B shows the inflated cuff reaching its pressure plateau A before the volume of the inflated cuff is sufficiently large to cause circumferential contact with the trachea. Circumferential contact is achieved at volume value T after which additional increases in intra-cuff pressure are attributable to the inner lining of the trachea resisting further expansion of the cuff. Once circumferential contact is achieved, additional inflation of the cuff causes the intra-cuff pressure to increase from value A to value B along the generally linear pressure-volume curve x. The pressure-volume curve w, generated by subtracting the value A of the pressure plateau from curve x, represents the mucosal pressure. It should be noted that the mucosal pressure is zero until circumferential contact between the cuff and the inner lining of the trachea is achieved.

The volume axis shown in FIG. 2B could alternatively be represented in terms of the diameter of the inflated cuff. To reliably use the above-described method for measuring the mucosal pressure, the cuff should have the following characteristics. The diameter of the inflated cuff corresponding to volume C should be smaller than the smallest expected tracheal diameter (this insures that the cuff reaches its pressure plateau prior to making circumferential contact with the inner lining of the trachea). Also, the diameter of the inflated cuff corresponding to volume D should be larger than the largest expected tracheal diameter (this insures that the inflated cuff makes circumferential contact with the trachea before unrestricted inflation of the cuff could cause the intra-cuff pressure to exceed the pressure plateau). Also, the diameter of the inflated cuff corresponding to volume D should be sufficiently larger than the largest expected tracheal diameter to permit cuff 2 to form a seal (e.g., with a mucosal pressure of 30 centimeters of water) with the largest expected trachea prior to reaching volume D.

Since the inner diameter of the human trachea is relatively small (e.g., from about 1.5 to about 2.5 centimeters in an adult), it is generally difficult to construct the cuff of an ETT such that its diameter, when the pressure plateau is initially reached, is reliably smaller than the smallest expected tracheal diameter. Latex however has several advantageous features that suggest its use as a cuff material. For example, one way to reduce the diameter of a latex cuff at which the pressure plateau is reached, and thereby attempt to ensure that the pressure plateau is reached prior to achieving circumferential contact between the cuff and the inner lining of the trachea, is to longitudinally pre-stretch the latex cuff prior to attaching it to the ETT as taught in Young et al. in GB 2324735. Additionally, latex has been shown to provide a superior seal against the trachea as compared with conventional more inelastic materials since no longitudinal wrinkles are formed in the cuff material that would allow foreign matter to pass through the cuff seal and thereby enter the lungs.

However, the use of latex in medical environments and for medical devices has become increasingly scrutinized, because many people experience an allergic reaction to latex material. The potential allergic reaction can be further complicated by the possibility that the patient may be on a respirator and is possibly in an immuno-compromised state. Additionally, latex material tends to degrade more rapidly than other medical grade material. Thus, it is advantageous to find another material possessing similar characteristics to latex but lacking its allergenic potential and limited shelf-life.

Silicone has been suggested as a suitable cuff material for ETTs. However, unlike latex, silicone does not adhere well to other plastic materials, such as PVC. For at least this reason, ETTs made using a PVC tube and a silicone balloon have not been used in the prior art.

One solution is to make both the cuff and the tube out of silicone. However, this has disadvantages that have not been overcome in the prior art. For example, since silicone is less stiff than for example PVC, a silicone endotracheal tube requires a greater wall thickness than a tube made of another material. Since the inner diameter of the tube is generally determined by the desired airflow characteristics of the tube, the larger wall thickness has the disadvantage of necessitating a larger outer diameter. Because the tube has a larger outer diameter, it is more difficult to have a cuff attached to the tube reach its pressure plateau prior to circumferentially contacting the wall of the trachea. If a silicone tube with thinner wall thickness is used, the tube tends to collapse in either the tubular portion proximal the cuff or at the cuff itself. In either case, if the tube collapses, there is a possibility that the patient will not receive the medical gasses from the ventilator.

Accordingly, there remains a need for an ETT having a cuff with the advantageous features of latex (e.g., providing ability to measure mucosal pressure and providing superior seal) without the disadvantages of latex (e.g., allergic potential and limited shelf life).

SUMMARY OF THE INVENTION

These and other objects are provided by an improved ETT. In one embodiment, the ETT includes a silicone tubular member and an inflatable silicone cuff, or balloon, which is attached to the tubular member near its distal end. Upon inflation, the silicone cuff reaches its pressure plateau before the cuff is large enough to make circumferential contact with the inner lining of the smallest normal human trachea with which the ETT will be used. For example, in an adult size, the cuff may reach its pressure plateau when its diameter is less than one and a half centimeters (i.e., less than 1.5 cm). The tubular member may define a first zone and an adjacent second zone, the first zone being a zone of reduced diameter, such that an outer diameter of at least a portion of the first zone is less than an outer diameter of the second zone. The cuff may be attached to the tubular member such that the cuff extends over at least a portion of the first zone. The cuff may extend over the entire first zone and part of the second zone.

The material used to form the cuff may be pre-stretched before it is attached to the tubular member. For example, the cuff may be formed from a tube of elastic material, which is characterized by a natural, resting, un-stretched diameter (i.e., the un-stretched diameter is the diameter when the cuff is in an un-stretched condition). The cuff may be configured so that its un-stretched diameter is smaller than the diameter of the portion of the tubular member to which the cuff is attached, such that when the cuff is mounted to the tubular member, the cuff is circumferentially stretched even when fully deflated.

In other aspects, the cuff material may have a Shore A hardness of about 10. Also, the tubular member may be reinforced with a spiral wire, or reinforcing member. The first zone of the tubular member, or the zone of reduced diameter, may also define a textured outer surface. The textured outer surface may take the form of grooves, e.g., spiral or linear, cut into the outer surface.

In addition to ETTs, the present invention can be applied to tracheostomy tubes which are inserted into a patient's airway via a tracheostomy—a hole cut into the front of the neck, opening into the trachea. The length of a tracheostomy tube is substantially shorter than an ETT but the same need for sealing between the cuff and the trachea is present. Additionally, the present invention may be applied to dual lumen endotracheal tubes in which the distal end of the ETT branches into two tubes, one for each lung.

In another aspect, instead of being made from silicone, the tubular member may be made of a plastic material such as PVC. In this embodiment, the plastic tubular member may also define a zone of reduced outer diameter where the cuff is disposed. A shrink-wrap annulus may be used at either or both ends of the cuff to secure the cuff to the tubular member. The location of the shrink-wrap material in the reduced diameter portion minimizes the possibility that the shrink-wrap material will be forced to slide off the ends of the cuff as it expands, since it will be prevented from doing so by abutting against the larger diameter part of the tubular member, which thus tends to hold it in place. Moreover, the relatively low pressures to which the cuff is inflated also ensures that the shrink wrap material maintains the cuff secured to the tubular member.

These and other features of the invention will be apparent upon reviewing the detailed description of the invention when read with the accompanying illustrations.

BRIEF DESCRIPTION OF THE DRAWINGS

FIG. 1A is a drawing of a prior art ETT.

FIG. 1B shows a magnified sectional view of the ETT taken along the line 1B-1B as shown in FIG. 1A.

FIG. 3A shows an ETT constructed according to the invention.

DETAILED DESCRIPTION OF THE INVENTION

FIG. 3A shows an ETT 19 constructed according to the invention. ETT 19 includes a hollow tube, or tubular member, 19a and a cuff, or balloon, 20 mounted near the distal end of tube 19a. Also, in ETT 19, hollow tube 19a and cuff 20 are both made of silicone. The Durometer (or hardness) of the silicone used to fabricate hollow tube 19a may be about 80 Shore A. A suitable source of silicone for fabricating tube 19a is Dow Corning, Midland, Mich., or Wacker Silicone in Germany. Tube 19a may be about 30-40 cm in length for adult sizes.

Use of a silicone cuff 20 is advantageous because, as discussed above, silicone does not have the allergic effects associated with latex, and silicone has a longer shelf life than latex. Use of a silicone tube 19a facilitates attachment of cuff 20 to the tube 19a since methods of adhering silicone to silicone are well known in the art. Also, as discussed below, dimensions of the hollow tube 19a and the cuff 20 are adjusted so as to advantageously provide an adequate air supply to the patient's lungs during IPPV and so as to insure that the cuff 20 reaches its pressure plateau before making circumferential contact with the inner lining of the trachea. Accordingly, ETT 19 facilitates measurement of the mucosal pressure and further facilitates avoidance of excessive mucosal pressures. Also, use of the silicone cuff 20 provides improved seals with the trachea and avoids the wrinkles and microleaks associated with inelastic cuffs.

Figure 3B:
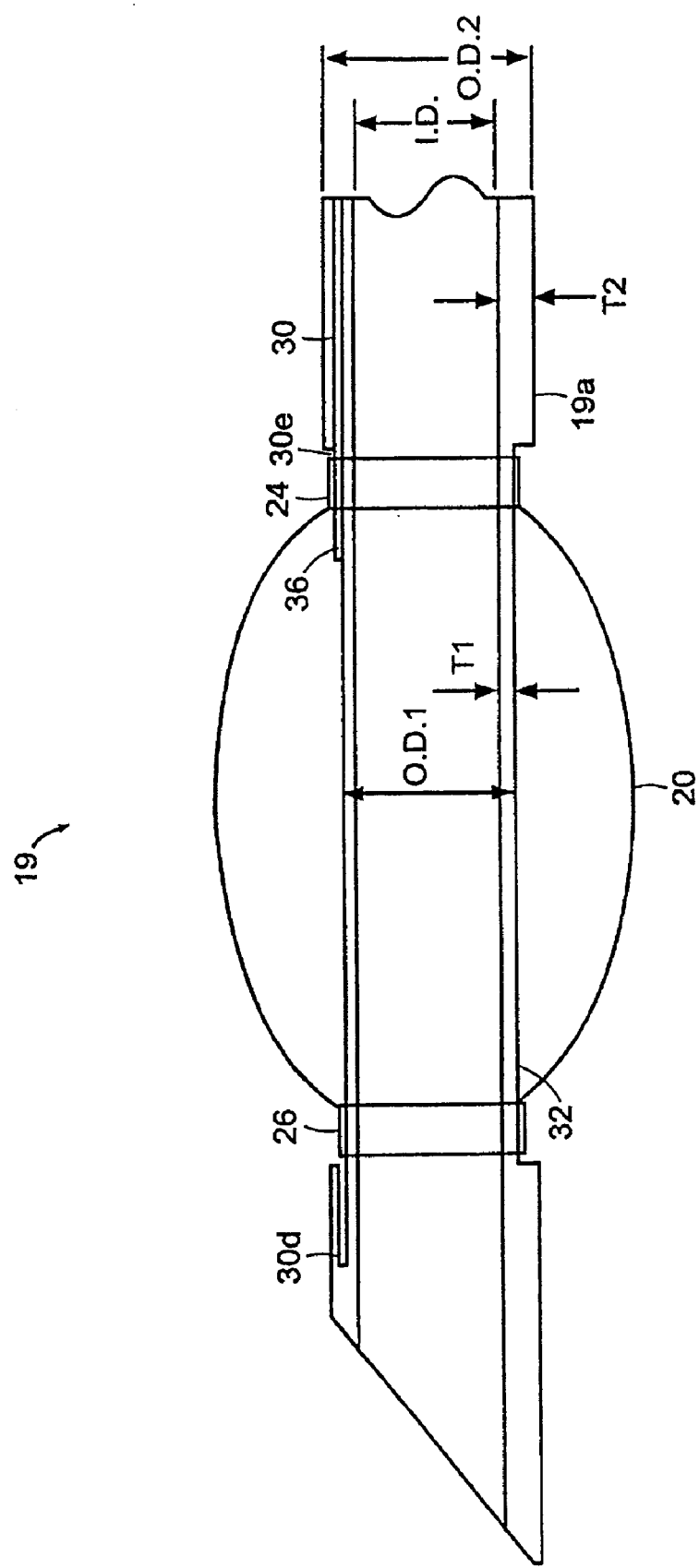
FIG. 3B is a magnified sectional side view showing a region of reduced diameter in an ETT constructed according to the present invention.

In ETT 19, the cuff 20 is mounted to hollow tube 19a in a region, or zone, 32 of reduced diameter. That is, in region 32, the outer diameter of tube 19a is reduced as compared with the outer diameter at other portions of tube 19a. FIG. 3B shows a magnified view of the region 32 of reduced diameter. As shown, the outer diameter of region 32, OD1, is reduced from the outer diameter of the rest of hollow tube 19a, OD2. In contrast, the inner diameter ID of hollow tube 19a (or the diameter of the airway lumen) is substantially constant from the proximal end to the distal end of hollow tube 19a. As a result of the differing outer diameters, the thickness TI of the wall of hollow tube 19a in region 32 is less than the thickness T2 of the wall of the remainder of hollow tube 19a. An inflation lumen 30 is defined in the wall of hollow tube 19a in the regions where the wall thickness is T2 (i.e., in regions outside the zone 32 of reduced diameter).

As shown, cuff 20 is mounted to tube 19a at extreme ends of region 32 at locations 24 and 26 (i.e., locations 24 and 26 are adjacent to the junctions between region 32 and other portions of the tube outside of region 32). Typically, for an adult size ETT, the distance between the mounting locations 24 and 26 is about three to five centimeters. Also, a relatively short rigid extension tube 36 extends from inside lumen 30, through cuff mounting location 24, and into the interior volume of cuff 20. Accordingly, inflation and deflation of cuff 20 can be controlled by an air supply, such as a syringe, coupled to the proximal end of inflation lumen 30 (near the proximal end of hollow tube 19a).

Since hollow tube 19a is made from silicone, the thickness of the tube wall T2 is greater than would be required if the tube were made of a more rigid material such as PVC. Accordingly, for a given inner diameter, ID, the outer diameter OD2 of hollow tube 19a is greater than the outer diameter that would be required if hollow tube 19a were made of PVC. The larger outer diameter OD2 of hollow tube 19a increases the difficulty of insuring that a cuff attached to tube 19a will reach its pressure plateau prior to making circumferential contact with the inner lining of the trachea. However, to compensate for the increased tube outer diameter, which is a consequence of using silicone to fabricate tube 19a, the tube 19a is provided with region 32 of reduced diameter. Attaching cuff 20 to the region 32 of reduced diameter increases the amount by which the cuff expands before it makes circumferential contact with the inner lining of the trachea and thereby facilitates insuring that cuff 20 reaches its pressure plateau prior to making such circumferential contact.

In one example embodiment of an adult size ETT, the inner diameter ID of tube 19a is about seven millimeters, the wall thickness T2 is about 1.625 millimeters, the wall thickness T1 in region 32 is about 1.0 millimeters, the outer diameter OD1 of the tube 19a in region 32 is about nine millimeters, and the outer diameter OD2 of the majority of tube 19a is about 10.25 millimeters. The pressure plateau of cuff 20 is about thirty to thirty five centimeters of water and is reached when the cuff diameter is less than the smallest expected adult tracheal diameter (e.g., less than about 1.5 centimeters).

In yet another example embodiment of an adult size ETT, the inner diameter ID of tube 19a is about eight millimeters, the wall thickness T2 is about 1.625 millimeters, the wall thickness T1 in region 32 is about 1.125 millimeters, the outer diameter OD1 of the tube 19a in region 32 is about 10.25 millimeters, and the outer diameter OD2 of the majority of tube 19a is about 11.25 millimeters. Again, the pressure plateau of cuff 20 is about thirty to thirty five centimeters of water and is reached when the cuff diameter is less than the smallest expected adult tracheal diameter (e.g., less than about 1.5 centimeters).

As noted above, inflation lumen 30 is defined in the wall of hollow tube 19a in the regions where the wall thickness is T2 (i.e., in regions outside the region 32 of reduced diameter). The presence of inflation lumen 30 in the wall of hollow tube 19a is one aspect of the ETT 19 that limits the tube's minimum wall thickness. Advantageously, the lumen 30 does not extend beyond the region 32 of reduced diameter, e.g., the lumen extends from near the proximal end of the tube 19a to the reduced diameter portion 32. A relatively short rigid hollow tube 36 is inserted within the lumen 30 and extends through the balloon mounting location 24 to provide fluid communication between lumen 30 and the interior of cuff 20.

If the wall thickness T1 of the region 32 of reduced diameter is too thin, the intra-cuff pressure of cuff 20 (which is circumferentially applied to the outer wall of region 32, and in effect squeezes region 32 inwards), may be sufficient to cause the region 32 of reduced diameter to collapse. Such collapse of any portion of hollow tube 19a is of course not desired since it may occlude the airway lumen provided by the ETT thereby preventing adequate ventilation of the lungs. One method of preventing such collapse is to fabricate the cuff 20 from silicone having a durometer of about 10 Shore A. Use of a silicone cuff with such a hardness allows the pressure plateau to occur as low as thirty to thirty five centimeters of water, a pressure which will not harm the tracheal mucosa or allow the tube to collapse under normal operating conditions.

Figure 4:
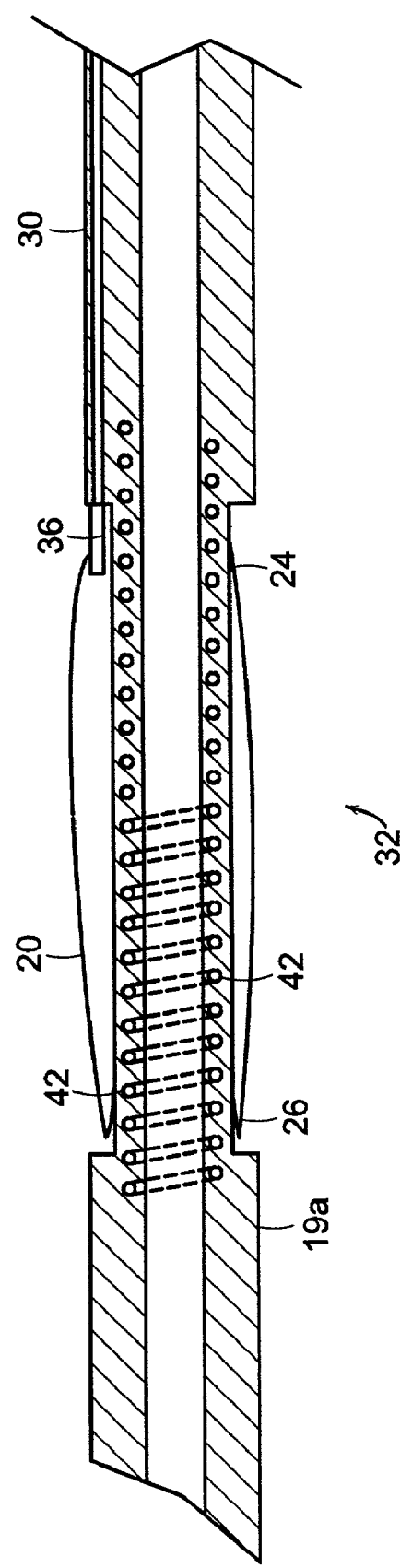
FIG. 4 is a sectional side view showing a region of reduced diameter with a reinforced tube in an alternative embodiment of an ETT constructed according to the present invention.

FIG. 4 illustrates another method of preventing collapse of hollow tube 19a, and in particular, of preventing collapse of region 32 of reduced diameter. FIG. 4 shows a magnified sectional view of region 32, when cuff 20 is deflated, of an alternative embodiment of ETT 19 constructed according to the invention. In the embodiment illustrated in FIG. 4, a spiral reinforcing wire, or other stiffening element, 42 is incorporated into the wall of hollow tube 19a. Reinforcing wire 42 provides radial strength to the hollow tube 19a and increases the tube's crush strength so that tube 19a will not collapse when the cuff 20 is inflated. Preferably, reinforcing wire 42 is located near the inside surface of hollow tube 19a. Providing a reinforcing wire at such a location facilitates allowing both the reinforcing wire 42 and the air supply lumen 30 to exist in the same tube 19a. Reinforcing wire 42 may extend along the entire length of hollow tube 19a, or alternatively, may be disposed only proximal the region 32 of reduced diameter.

It will be appreciated that many manufacturing methods may be used for fabricating tube 19a such that it includes reinforcing wire 42. For example, a reduced diameter tube (i.e., a tube having an inner diameter ID equal to the desired inner diameter of tube 19a and an outer diameter less than the outer diameter OD1 of region 32) may be extruded and then the reinforcing wire 42 may be disposed on the outer surface of the tube. A second tube may then be applied, or extruded over the reduced diameter tube and the wire. The second, or outer, tube may be heated and bonded with the reduced diameter tube to create a single tube 19a. The region 32 of reduced diameter may then be formed by removing material from a portion of the outer surface of the tube. For example, the region 32 may be formed by placing the tube 19a on a lathe and cutting material away from a portion of the outer surface of the tube. Such manufacturing techniques may be used to form the region 32 of reduced diameter regardless of whether a reinforcing wire is incorporated into the tube.

Referring again to FIG. 3B, it can be seen that tube 19a may be fabricated such that inflation lumen 30 initially extends from the proximal end of tube 19a to a location 30d near the distal end of tube 19a. Using a lathe or other device for cutting material away from a portion of tube 19a so as to form region 32 of reduced diameter automatically connects inflation lumen 30 to the region 32, at location 30e, as long as enough material is removed from the outer portion of the tube to expose lumen 30. Rigid tube 36 may be used to thereafter couple inflation lumen 30 to the interior volume of cuff 20 as discussed above.

Figure 5:
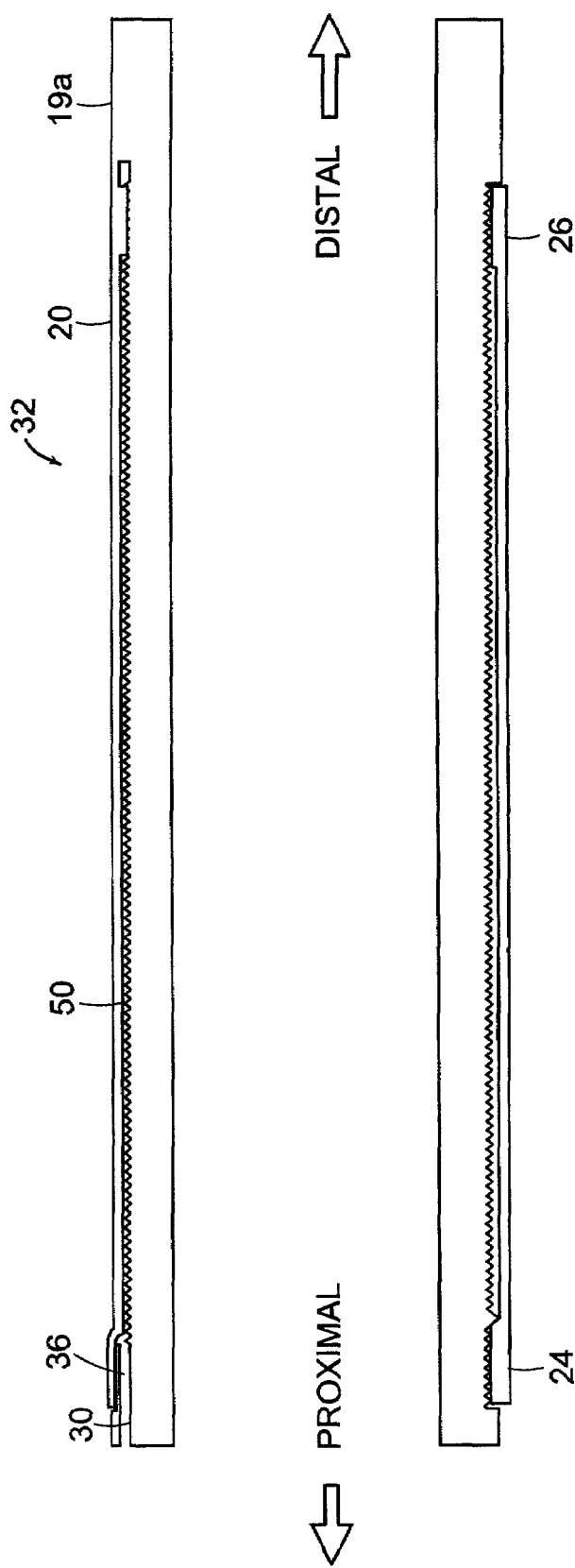
FIG. 5 is a sectional side view showing a region of reduced diameter with a textured outer surface in another alternative embodiment of an ETT constructed according to the invention.

FIG. 5 shows a magnified sectional view of region 32 of reduced diameter, when cuff 20 is deflated, of another embodiment of ETT 19 constructed according to the invention. As shown, the outer surface of tube 19a in the region 32 of reduced diameter is characterized by a texture 50, or a roughening. Providing texture 50 advantageously reduces the likelihood that the cuff 20 will stick to the tube 19a. It is generally not desirable for any portion of cuff 20 (other than at locations 24, 26, where cuff 20 is bonded to tube 19a) to stick to the outer surface of tube 19a because such sticking generally causes the cuff to inflate non-uniformly. Non-uniform inflation of cuff 20 is undesirable because it generally results in formation of a less than optimal seal with the trachea.

In one preferred embodiment, the texture 50 has the form of a threaded surface (e.g., as in the threads of a screw) and comprises one or more spiral grooves cut into the outer surface of tube 19*a*. In one embodiment, the grooves are 0.5 millimeters wide and 0.2 millimeters deep. The grooves may be cut, for example, using a high speed lathe. One advantage of having texture 50 be a spiral groove, is that this texture rapidly and evenly distributes air introduced from lumen 30 to the entire interior surface of the cuff, and thereby provides for uniform inflation of the cuff 20. However, it will be appreciated that textures 50 other than spiral grooves may be used as well. For example, texture 50 can comprise longitudinal rather than spiral grooves, or a random or pseudo random roughening.

Figure 6:
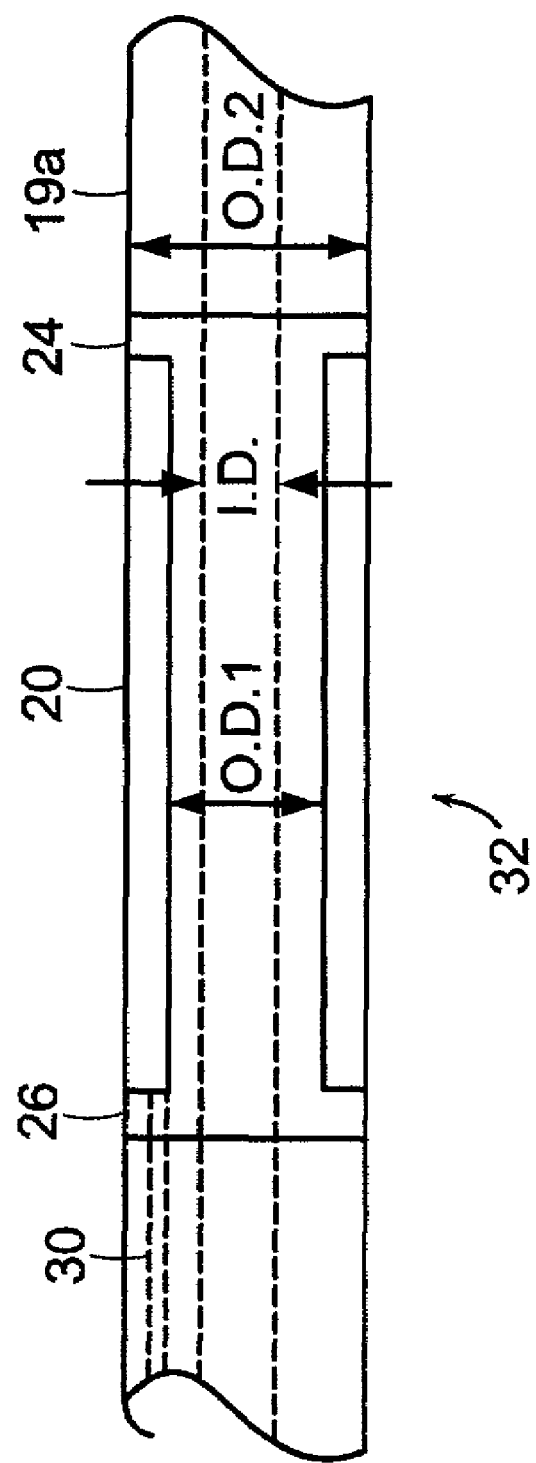
FIG. 6 is a sectional side view showing a region of reduced diameter in another alternative embodiment of an ETT constructed according to the invention, in which the cuff is attached to the tube outside of the region of reduced diameter.

FIG. 6 shows a magnified view of region 32 of reduced diameter, when cuff 20 is deflated, of yet another embodiment of ETT 19 constructed according to the invention. In previously discussed embodiments, the locations 24, 26, where cuff 20 is attached to tube 19*a*, are in the region 32 of reduced diameter (i.e., locations 24, 26 were located where the outer diameter of the tube 19*a* is OD1). However, as shown in FIG. 6, the locations 24, 26 may be located outside of region 32 (i.e., locations 24, 26 may be located where the outer diameter of tube 19*a* is OD2). In this embodiment, the semi-rigid tube extension 36 (shown, e.g., in FIG. 3B) may be eliminated. The embodiment illustrated in FIG. 6 may be used for example when the material used to form cuff 20 is pre-stretched as discussed in more detail below.

It may be desirable to tailor the region 32 of reduced diameter, and possibly portions of the tube 19*a* adjacent to region 32, to provide tube 19*a* with a smooth surface so as to minimize irritation to the patient' natural airway during introduction and removal of ETT 19. For example, in the embodiment illustrated in FIG. 6, the outer diameter of ETT 19 may increase slightly at locations 24, 26 thereby disturbing, or providing a "step" in, the otherwise smooth outer surface of tube 19*a*. To eliminate this step, it may be desirable to remove a small portion of the outer surface of tube 19*a* at locations 24, 26, so that when cuff 20 is attached, the outer surface of ETT 19 is smooth and does not include a stepped surface at locations 24, 26. Similarly, in the embodiments illustrated in FIGS. 3B, 4, and 6, it may be desirable to taper the outer surface of tube 19*a* adjacent region 32 so as to provide a smoothly changing outer diameter rather than a step.

Figure 2B:
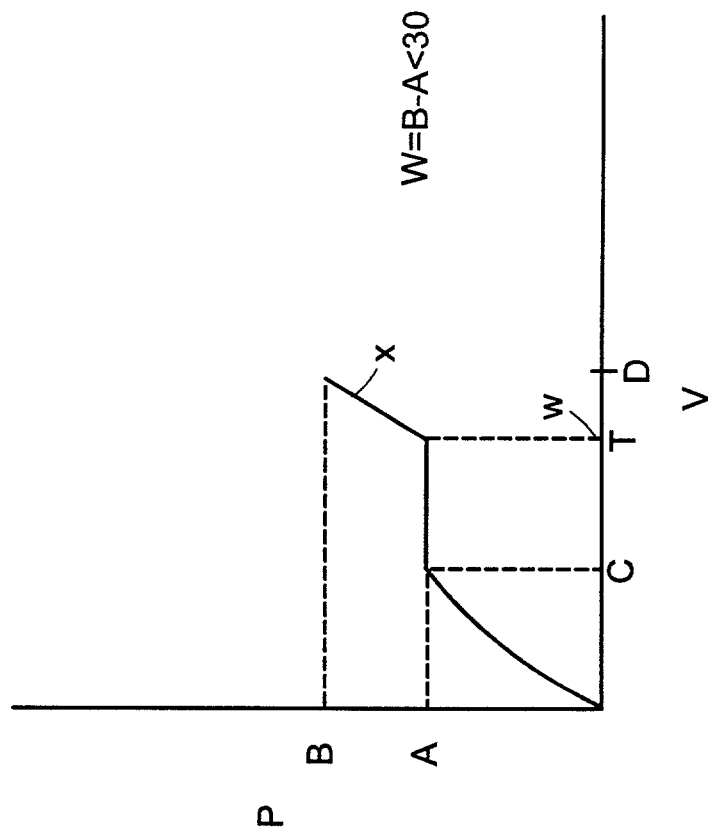
FIGS. 2a and 2b show prior art Pressure vs. Volume diagrams.
Figure 2A:
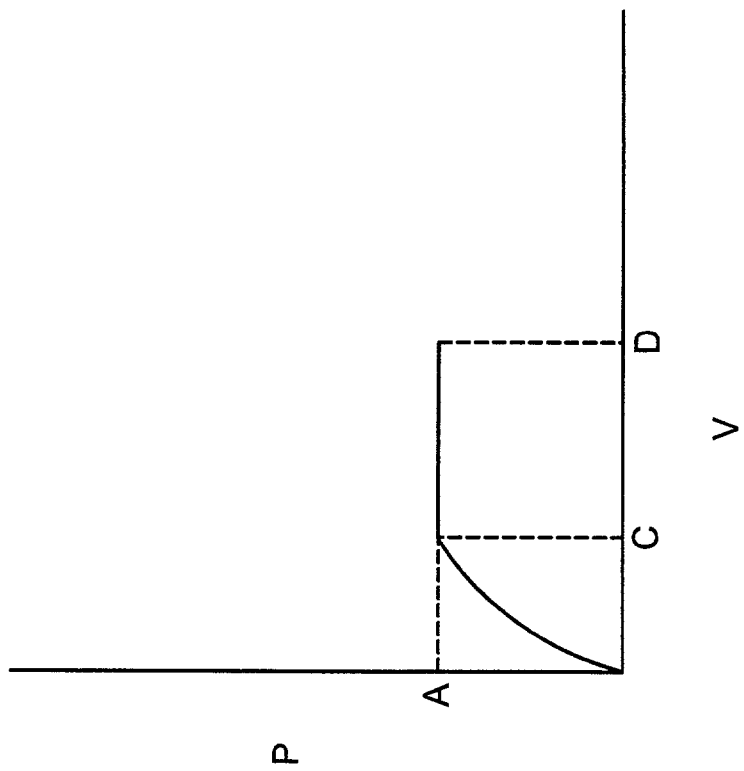

As discussed above, inclusion of region 32 increases the amount that cuff 20 will expand, and thereby increases the likelihood that cuff 20 will have reached its pressure plateau, prior to making circumferential contact with the inner lining of the trachea. Accordingly, inclusion of region 32 of reduced diameter facilitates measurement of the mucosal pressure and further facilitates avoidance of excessive mucosal pressures, since the mucosal pressure generated by a silicone cuff may be measured using the procedure discussed above in connection with FIG. 2B. Another method of increasing the likelihood that cuff 20 will have reached its pressure plateau prior to making circumferential contact with the inner lining of the trachea is to prestretch the cuff 20 prior to mounting it to tube 19*a*, so that the cuff material is in a stretched state (i.e., beyond its natural resting dimensions) even when the cuff is fully deflated. Such stretching, or prestretching, reduces the additional amount that the cuff must stretch before reaching the pressure plateau. There is a limit to how much prestretching should be applied to the cuff. If the cuff is prestretched too much, the cuff will not be able to expand to the proper diameters safely. Moreover, if additional cuff material is used for the cuff so that the cuff may become able to expand to the appropriate diameters, attachment points which affix the cuff to the tube may be too far apart. As presently conceived, the percent stretching desirable for the cuff is between 50 and 100 percent. That is, if a 3 centimeters linear length of cuff is stretched to 6 centimeters, the resultant stretch would be 100 percent. Although stretching is clearly desirable, excess stretching can reduce the shelf life of the cuff. Accordingly, one skilled in the art will recognize that the optimal amount of stretching in a design includes consideration of the shelf life.

In one method of stretching the cuff prior to final mounting, a cuff, which may be a tubular piece of elastic material, may be mounted onto tube 19*a* in an unstretched manner and then inflated. The inflated cuff is then pulled axially along the tube 19*a* to invaginate part of the cuff on itself so that part of the cuff is "doubled-up." The part of the cuff that is doubled-up is then secured to the tube. Thus the cuff is mounted on the tube 19*a* in a stretched manner. This increases the likelihood that the pressure plateau is achieved before the cuff makes circumferential contact with the inner lining of the trachea. Pre-stretching the cuff also reduces the likelihood that the cuff will stick to the tube.

Figure 7A:
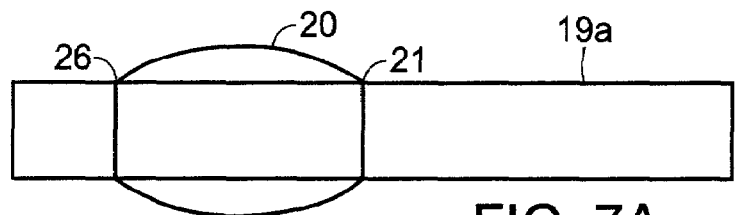
FIGS. 7A-7C illustrate a method according to the invention of longitudinally pre-stretching cuff material while attaching a cuff to an ETT.
Figure 7B:
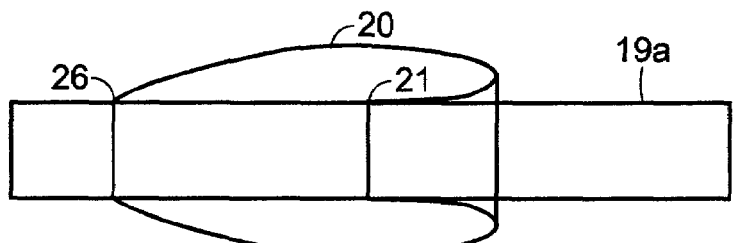
Figure 7C:
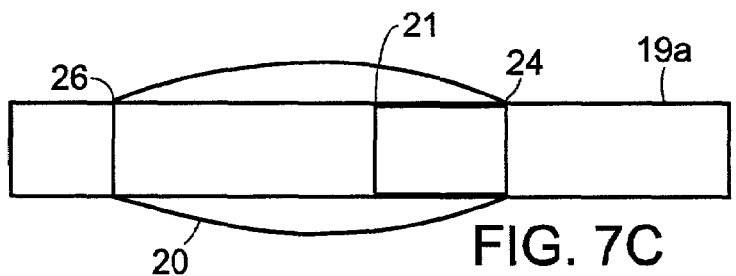

FIGS. 7A-7C briefly illustrate this method of pre-stretching the cuff 20. As shown in FIG. 7A, cuff material 20 is initially attached to tube 19*a* and inflated. At this point, the left end of the cuff is attached to tube 19*a* at location 26 and the right end of the cuff is attached to the tube 19*a* at location 21. As shown in FIG. 7B, the cuff is then pulled longitudinally to the right so as to stretch the cuff material. This step of stretching the cuff material by pulling it to the right may be accomplished for example manually. Pulling the cuff to the right as shown in FIG. 7B results in all of the cuff material to the right of the attachment point at location 21 becoming "doubled-up". As illustrated in FIG. 7C, the cuff is then squeezed inwardly towards the tube 19*a* so that the right end of the cuff material contacts the tube 19*a*, at location 24. The right end of the cuff material is then attached to the tube 19*a* at location 24. This results in all cuff material between locations 24 and 26 being, in effect, longitudinally pre-stretched. For convenience of illustration, the region 32 of reduced diameter is not shown in FIGS. 7A-7C, however, it will be appreciated that the steps illustrated therein may be performed so as to result in having the cuff 20 located within region 32.

Figure 8A:
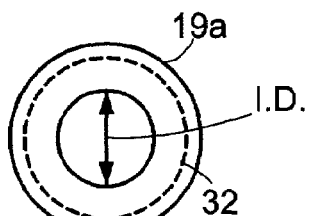
FIG. 8A shows a sectional side view of one embodiment of an ETT constructed according to the invention, the view being taken in the general direction of line 9-9 as shown in FIG. 3A.
Figure 8B:
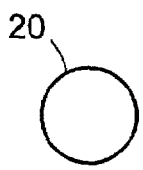
FIG. 8B shows a sectional side view of a tube of elastic material used to form a cuff for the tube shown in FIG. 8A, the elastic material being circumferentially stretched while forming the cuff.

The method described above in connection with FIGS. 7A-7C results in pre-stretching the cuff material in a longitudinal direction prior to mounting the cuff 20 to tube 19*a*. As an alternative to longitudinal stretching, the cuff material may also be stretched circumferentially prior to mounting cuff 20 to tube 19*a*. FIGS. 8A and 8B illustrate such circumferential prestretching. FIG. 8A shows a sectional side view of tube 19*a* of an ETT constructed according to the invention, the side view being taken in the general direction of line 9-9 as shown in FIG. 3B. In FIG. 8A, the circle labeled 19*a* represents the outer periphery of the majority of hollow tube 19*a* (the outer diameter of which is OD2); the dashed circle labeled 32 represents the outer periphery of the region 32 of reduced diameter of tube 19*a* (the outer diameter of which is OD1); and the circle interior to 32, the diameter of which is labeled ID, represents the interior lumen, or airway passage, which extends from the proximal end to the distal end of hollow tube 19*a*. In FIG. 8B, the circle labeled 20 represents a tube of elastic material, seen in a cross section taken in the same general direction as the cross section of FIG. 8A, that will be used to form cuff 20. For convenience of illustration, the inflation lumen 30 is not shown in FIG. 8A. As shown, when the cuff material is in its natural resting (unstretched) state, its diameter is less than that of region 32. So, placing the cuff material over tube 19*a* and locating it in region 32 advantageously results in circumferentially pre-stretching the cuff material. It will be appreciated that the cuff material may also be pre-stretched both circumferentially and longitudinally.

Figure 9:
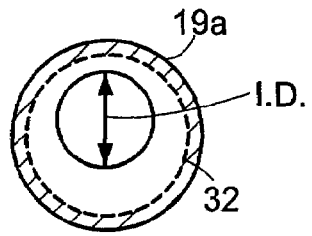
FIG. 9 shows a sectional side view, taken in the direction of line 9-9 as shown in FIG. 3B, of an alternative embodiment of an ETT constructed according to the invention having an eccentric airway lumen.

FIG. 8A shows the airway passage (the diameter of which is ID) as being concentrically located within tube 19*a*. However, it may be advantageous to form the airway passage so that it is eccentrically located within tube 19*a*. FIG. 9 shows an example of such an eccentrically located airway lumen. The eccentricity enables the tube 19*a* to bend more easily along the portion of the tube with the increased thickness. The eccentricity can help reduce the pressure applied to the trachea when the ETT 19 is in place. As with FIG. 8A, for convenience of illustration, the inflation lumen 30 is not shown in FIG. 9.

As discussed above, tube 19*a* is preferably fabricated from silicone. However, other materials may be used as well. In particular, it may be advantageous to form tube 19*a* from a material that is harder than silicone such as PVC. Use of a harder material such as PVC allows the outer diameter OD1 of the tube 19*a* outside the region 32 to be reduced as compared with that of a silicone tube. In one embodiment, a region 32 of reduced diameter is formed in a PVC tube 19*a* by reducing the external diameter by 10% over the length of the tube onto which the cuff is mounted.

As discussed above, adhering a silicone cuff 20 to a PVC tube 19*a* is more difficult than adhering a silicone cuff to a silicone tube. However, shrink wrap material may be used to attach a silicone cuff 20 to a PVC tube 19*a*. The shrink wrap material may be configured for example as a tube or annular ring, which is shrunk over the two materials so as to hold the cuff 20 to the tube 19*a*. When shrink wrap material is used to hold cuff 20 to tube 19*a*, the cuff 20 may tend to roll or slide in a longitudinal direction when the cuff is inflated. For example, referring to FIG. 3B, at location 24 the cuff 20 may tend to roll or slide to the left (towards the proximal end of the ETT 19) upon inflation. One advantage of placing locations 24, 26 within the region 32 of reduced diameter, is that any such rolling or sliding will cause the shrink wrap material to abut into the thicker part of the tube 19*a* (i.e., where the wall thickness is T2) and this abutment tends to hold the shrink wrap material in place. Additionally, since shrink wrap material adds thickness, it can be used to minimize or eliminate a "step" or rough spot, at the junction of region 32 with the rest of tube 19*a*. Accordingly, it can be advantageous for locations 24, 26 to be at the extreme ends of region 32 so that the locations 24, 26 abut the thicker part of the tube 19*a*. However, as shown in FIG. 6 it can also be advantageous for locations 24, 26 to be outside of region 32. Alternatively, it is also possible to have one of locations 24, 26 be within region 32 and have the other one be outside of region 32.

In addition, or as an alternative, to use of shrink wrap material, other methods, such as laser welding, heat welding, or use of adhesives, may be used for attaching cuff 20 to hollow tube 19*a*. However, use of shrink wrap material is preferred for adhering a silicone cuff to a PVC tube, whereas other methods such as welding are preferred for adhering a silicone cuff to a silicone tube.

The above description is intended to provide a representative example of the device defined in the claims. Changes may be made in the apparatus disclosed above without departing from the scope of the invention recited in the claims. All the description contained above and shown in the drawing shall be interpreted in an illustrative and not in a limiting sense. For example, while ETTs have been discussed in detail, it will be appreciated that the invention may be applied to tracheostomy tubes as well. As such, the hollow tubes or tubular members used to form medical devices according to the invention need not be perfect tubes having uniform cross sections along their entire length. Rather, the tubular members may include pre-formed bends, or angles (as in the case of a tracheostomy tube). Also, the outer diameter of the tubular members need not be constant within the zone of reduced diameter or outside that zone. However, the outer diameter of at least a portion of the zone of reduced diameter will generally be smaller than the outer diameter of a portion of the tubular member adjacent to the zone of reduced diameter. Also, whereas several different methods and structures have been discussed individually (e.g., textured outer surface, reinforcing member, pre-stretching), it will be appreciated that they may be used alone or in combination. For example, an ETT constructed according to the invention may include a reinforcing wire, a zone of reduced diameter having a textured outer surface, and a pre-stretched cuff.

What is claimed is:

1. A medical device, comprising:
    A. a tubular member having a proximal end, a distal end, and a lumen extending though the member from the proximal end to the distal end, the member defining a first zone and a second zone, the first zone having a first attachment portion, a second attachment portion, and an interior portion disposed between the first and second attachment portions, the first attachment portion having a first outer diameter, the second attachment portion having a second outer diameter, the interior portion having an interior portion outer diameter, at least a portion of the second zone having a second zone outer diameter, said first, second and interior portion outer diameters each being smaller than the second zone outer diameter, the first and second zones being configured for insertion into a trachea of a human patient;
    B. an inflatable cuff attached to the first and second attachment portions of the tubular member, a thickness of the cuff being smaller than a difference between the second zone outer diameter and each of the first, second, and interior portion outer diameters, the cuff extending over the interior portion.

2. A medical device according to claim 1, the inflatable cuff comprising silicone.

3. A medical device according to claim 2, the cuff being characterized by a hardness of about ten Shore A.

4. A medical device according to claim 1, the cuff being characterized by an un-stretched diameter, the un-stretched diameter being smaller than at least one of the first outer diameter, the second outer diameter, and the interior portion outer diameter.

5. A medical device according to claim 1, the cuff upon inflation reaching a pressure plateau when a diameter of the cuff is less than about one and a half centimeters.

6. A medical device according to claim 1, the tubular member comprising silicone.

7. A medical device according to claim 1, the tubular member comprising poly-vinyl-chloride.

8. A medical device according to claim 1, the first zone comprising an outer textured surface.

9. A medical device according to claim 8, the textured surface comprising one or more spiral grooves.

10. A medical device according to claim 8, the textured surface comprising one or more grooves.

11. A medical device according to claim 1, a center of the lumen being offset from a center of the tubular member.

12. A medical device according to claim 1, the lumen being eccentrically located within the tubular member.

13. A medical device according to claim 1, a wall of the tubular member defining an inflation lumen, the inflation lumen being in fluid communication with an interior of the inflatable cuff.

14. A medical device according to claim 13, the device further including an extension tube extending from the inflation lumen to the interior of the inflatable cuff.

15. A medical device according to claim 1, further including a spiral reinforcing member extending along at least a portion of the tubular member.

16. A medical device according to claim 1, the cuff extending over the entire first zone.

17. A medical device according to claim 1, the cuff extending over the entire first zone and at least part of the second zone.

18. A medical device, comprising:
A. a silicone tubular member having a proximal end, a distal end, and a lumen extending through the member from the proximal end to the distal end, the member defining a first zone and a second zone, the first zone having a first attachment portion, a second attachment portion, and an interior portion disposed between the first and second attachment portions, the first attachment portion having a first outer diameter, the second attachment portion having a second outer diameter, the interior portion having an interior portion outer diameter, at least a portion of the second zone having a second zone outer diameter, said first, second and interior portion outer diameters each being smaller than the second zone outer diameter, the first and second zones being configured for insertion into a trachea of a human patient;
B. an silicone cuff attached to the first and second attachment portions of the tubular member, a thickness of the cuff being smaller than a difference between the second zone outer diameter and each of the first, second, and interior portion outer diameters, the cuff extending over the interior portion.

19. A medical device according to claim 18, wherein the cuff comprises material having a Shore A hardness of about 10.

20. A medical device according to claim 18, the cuff being characterized by an un-stretched diameter, the un-stretched diameter being smaller than at least one of the first outer diameter, the second outer diameter, and the interior portion outer diameter.

21. A medical device according to claim 18, a wall of the tubular member defining an inflation lumen, the cuff defining an inner space, the device further including an extension tube extending from the inflation lumen to the inner space defined by the cuff.

22. A medical device according to claim 18, further including a spiral reinforcing member.

23. A medical device according to claim 18, the cuff extending over the entire first zone.

24. A medical device according to claim 18, the cuff extending over the entire first zone and at least part of the second zone.

25. A method of fabricating a medical device, comprising:
A. providing a tubular member defining an axis, the member having a proximal end, a distal end, and a lumen extending through the member from the proximal end to the distal end, the member defining a first zone and a second zone, at least a portion of the first zone having a first outer diameter, the second zone having a second outer diameter, the first outer diameter being smaller than the second outer diameter, the first zone being adjacent to the second zone, the first and second zones being configured for insertion into a trachea of a human patient;
B. providing elastic material, the elastic material defining a generally tubular shape;
C. disposing at least a portion of the tubular member within the elastic material;
D. sealing a first portions and a second portion of the elastic material to the tubular member so that the elastic material between the first portion and the second portion encloses a first part of the first zone;
E. stretching the elastic material in a direction parallel to the axis to cause a third portion of the elastic material to surround a second part of the first zone, the second part being adjacent to the first part, the second portion of the elastic material defining a boundary between the first and second parts of the first zone of the tubular member; and
F. sealing a part of the third portion of the elastic material to the tubular member, the elastic material between the first portion and the sealed part of the third portion defining an inflatable cuff that encloses the first part of the first zone of the tubular member.

26. A method according to claim 25, the step of providing a tubular member comprising removing material from the tubular member to define the first zone.

27. A method according to claim 25, further comprising providing the first zone with a textured surface.

28. A method according to claim 25, further comprising providing the first zone with a textured surface comprising one or more spiral grooves.

29. A method according to claim 25, further comprising providing the first zone with a textured surface comprising one or more grooves.

30. A method according to claim 25, further comprising providing a spiral reinforcing member in the tubular member.

* * * * *